United States Patent [19]

Larner et al.

[11] 4,446,064

[45] May 1, 1984

[54] INSULIN MEDIATOR SUBSTANCE

[75] Inventors: Joseph Larner; Kang Cheng, both of Charlottesville, Va.; Gail Galasko, Johannesburg, South Africa

[73] Assignee: The University of Virginia Alumni Patents Foundation, Charlottesville, Va.

[21] Appl. No.: 218,075

[22] Filed: Dec. 19, 1980

[51] Int. Cl.³ .................................................. C07G 7/00
[52] U.S. Cl. .......................... 260/112 R; 260/112.5 R; 424/95
[58] Field of Search ...................... 260/112 R; 424/95; 260/112.5

[56] References Cited

U.S. PATENT DOCUMENTS 1,626,044  4/1927  Macy ................................. 424/95 X
3,326,763  6/1967  Antoniades ........................... 424/95

OTHER PUBLICATIONS

Fed. Proc. Fed. AM Soc. Exp. Biol. 33, 261 (1974), Larner et al.
Science, vol. 206, Dec. 21, 1979, pp. 1407–1408, Jarrett et al.
Science, vol. 206, Dec. 21, 1979, Larner et al.

Primary Examiner—Howard E. Schain
Attorney, Agent, or Firm—Oblon, Fisher, Spivak, McClelland & Maier

[57] ABSTRACT

An insulin mediator substance produced by the process comprising: contacting muscle tissue with insulin; deproteinizing the muscle tissue; removing the major nucleotides from the deproteinized muscle tissue; chromatographing the so-treated product on a Sephadex G-25 column using 0.05 N formic acid; and recovering the fraction wherein the major 230-nm absorbance peak corresponds with the ninhydrin-positive peak.

10 Claims, 2 Drawing Figures

INSULIN MEDIATOR SUBSTANCE

BACKGROUND OF THE INVENTION

1. Field of the Invention:

This invention relates to a chemical intermediate in the mechanism of action of insulin, and, the isolation and purification thereof.

2. Description of the Prior Art:

Macy, U.S. Pat. No. 1,626,044, describes the isolation of a non-proteinaceous anti-diabetic material from the pancreas which when added to a muscle extract containing enzymes, causes a disappearance of glucose.

Antoniades, U.S. Pat. No. 3,326,763, describes materials which affect the activity of bound insulin by releasing it from its bound complexes and thus making it more active.

A need therefor continues to exist for pharmaceutical methods of treating diabetes and/or increasing the activity of insulin therapy.

SUMMARY OF THE INVENTION

Accordingly, one object of the invention is to provide a substance suitable for the treatment of diabetes.

A further object of the invention is to provide a process for preparing a substance suitable for the treatment of diabetes.

Briefly, these objects and other objects of the invention as hereinafter will become more readily apparent can be obtained by providing a process for producing an insulin mediator substance comprising:

contacting muscle tissue with insulin;
deproteinizing the muscle tissue;
removing adenosine triphosphate, adenosine diphosphate and adenosine monophosphate from the deproteinized muscle tissue;
chromatographing the so-treated product on a Sephadex G-25 column using 0.05N formic acid; and
recovering the fraction wherein the major 230-nm absorbance peak corresponds with the ninhydrin positive peak; and by providing the product produced by the process.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
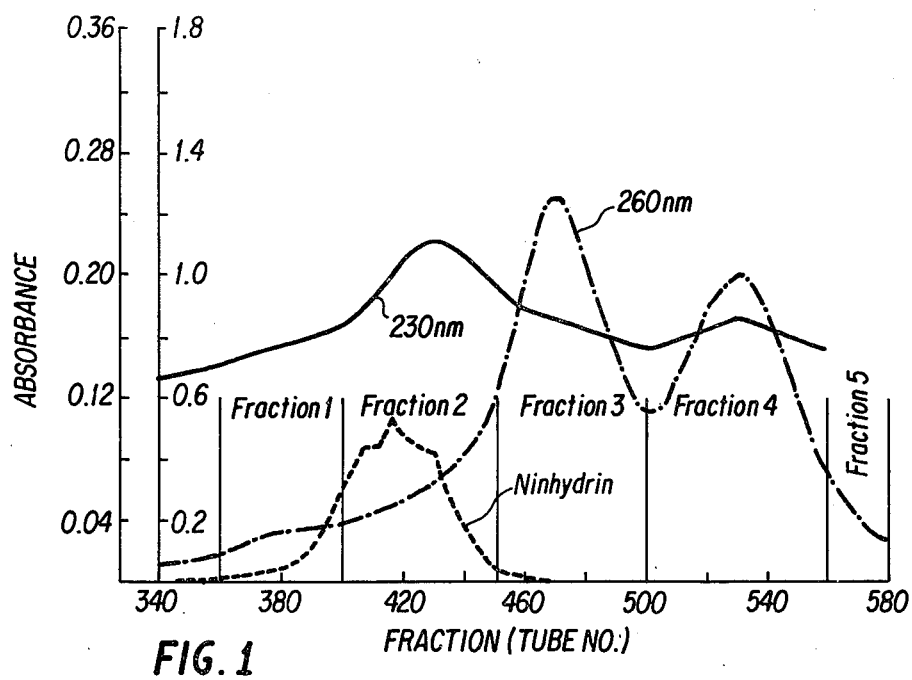
FIG. 1 is a Sephadex G-25 chromatogram of a muscle extract that had been deproteinized and from which the major nucleotides had been removed by paper chromatography.

A chemical intermediate in the mechanism of action of insulin has been proposed to explain the dissociation of insulin stimulation of glucose transport and glycogen synthesis (Larner, Diabetes, 21 (Suppl.2), 428 (1972)). In keeping with this hypothesis, two separate biochemical mechanisms have been established for the activation of glycogen synthase in the absence and in the presence of a transportable hexose (Lawrence, Jr. et al, J. Biol. Chem., 253, 2104 (1978); Oron, et al, Diabetes, 28, 365 (1979)). Prior to this work, it had already been established that insulin activated glycogen synthase with no change in basal cyclic adenosine monophosphate concentrations (Goldberg et al, Biochim. Biophys. Acta, 148, 665 (1967); Craig et al, Biochim. Biophys. Acta, 177, 213 (1969)). It has also been demonstrated that two high-molecular-weight materials each interacted in the insulin mechanism: (i) a pituitary diabetogenic peptide (25,000 daltons) which blocked the action of insulin, yet had weak agonist activity (Miller et al, Proc. Natl. Acad. Sci. U.S.A., 69, 2774 (1972)) and (ii) a human antibody receptor (150,000 daltons) which was indistinguishable from insulin in its agonist activity (Lawrence, Jr. et al, Mol. Cell. Biochem., 22, 152 (1978)). From the above, it is argued that insulin acted initially at the cell membrane (Larner et al, Cold Spring Harbor Symp. Quant. Biol., in press). Thus, it was reasonable to suppose that, as a result of the interaction, a mediator substance might be formed. To test this hypothesis, cyclic AMP-dependent protein kinase was used as a bioassay since it had been demonstrated that the protein kinase was present to a greater extent as as holoenzyme (Shen et al, Physiol. Chem. Phys., 2, 536 (1970)); Walaas et al, Eur. J. Biochem., 40, 465 (1973)), which was decreased in enzyme activity, and in its capacity to bind and be activated by added cyclic AMP after insulin treatment (Walkenbach et al, Mol. Cell, Biochem., 19, 31 (1978)). In 1974, it was first reported that an acid- and heat-stable substance that inhibits the cyclic AMP-dependent protein kinase is generated early in insulin action (Larner et al, Fed. Proc. Fed. Am. Soc. Exp. Biol., 33, 261 (1974)). It has now become possible to isolate and purify such a substance and to show that it also acts to activate the phosphoprotein phosphatase that converts glycogen synthase to its active form (insulin inactivating glycogen synthase (protein) kinase by conversion from independent (I) to dependent (D) form). This activation of the phosphoprotein phosphatase is in itself surprising since such activity was not tested for, in the impure material reported in 1974. Additionally, it has been demonstrated that this material, like added insulin, activates mitochondrial pyruvate dehydrogenase by dephosphorylation in a subcellular system in rat adipocytes (Jarett et al, Science, 206, 1407 (1979)). Because of its ability to mimic the action of insulin on cyclic AMP-dependent protein kinase, phosphoprotein phosphatase and pyruvate dehydrogenase, this peptide or peitide-like substance constitutes an insulin mediator.

This insulin mediator substance has been obtained from muscle tissue which has been contacted with insulin, any skeletal muscle tissue will suffice. The contacting with insulin may be conducted in vivo or in vitro. When in vivo contact is used, a host animal is injected with sufficient insulin so as to elicit a rapid response in blood glucose concentration and muscle tissue is then removed for further processing. When in vitro contact is used, e.g., muscle tissue obtained from an abattoir, sufficient insulin is contacted with the tissue so as to correspond with the amount of insulin necessary to elicit a rapid response in blood glucose concentration in the living animal, this can be readily determined through routine experimentation by those skilled in the art. The muscle tissue is then deproteinized, e.g., by heating at 100° C. so as to denature existing proteins and then removing the denatured proteins by filtration and/or centrifugation. Major nucleotides, e.g., adenosine triphosphate (ATP), adenosine diphosphate (ADP) and adenosine monophosphate (AMP), are then removed by any conventional means, e.g., paper chromatography or adsorption on charcoal. The resulting deproteinized material free of the major nucleotides is then chromatographed on a Sephadex G-25 column using 0.05N formic acid and the fraction wherein the major 230-nm absorbance peak corresponds with the ninhydrin-positive peak is recovered. Further purification of this fraction can be effected by thin layer chromatography or high voltage electrophoresis and then recovering the fraction which contains an inhibitor of cyclic AMP-dependent protein kinase.

The insulin mediator so recovered can be used in lieu of insulin or in combination therewith in the treatment of diabetes, the clinical effect being the same as insulin therapy. Administration of the insulin mediator can be effected by any conventional means for insulin therapy, e.g., injection, at dosages normally used in insulin therapy, as determined by the treating physician, although, in general, somewhat higher dose rates are indicated.

Having generally described this invention, a further understanding can be obtained by reference to certain specific examples which are provided herein for purposes of illustration only and are not intended to be limiting unless otherwise specified.

EXAMPLE 1

Rats were anesthetized with Nembutal for 15 minutes and then given insulin (4U/kg) or saline intravenously. Hind leg muscle was removed 5 minutes later, and was rapidly frozen in liquid nitrogen. Blood samples were taken for glucose analysis. In the animals receiving insulin the mean blood glucose concentration decreased from 151.7 to 102.9 mg/dl, and muscle glycogen synthase was activated from 26.1 to 35.7 percent independent of I form. Frozen powdered muscle (25g) was deproteinized by heating at 100° C. for 3 minutes, adding two volumes of acetic acid (pH 3.8) containing 0.1 mM EDTA and 0.1 mM cysteine at 100° C., and heating for 4 minutes. The mixture was cooled on ice, centrifuged to remove particulate denatured protein, and filtered through glass wool; the clear yellowish supernatant was lyophilized. The tan powder so-produced, was dissolved in 7.5 ml of 0.04N formic acid and streaked on washed Whatman 3 MM filter paper sheets (46 by 57 cm); two papers were used for each 25 g of original muscle. Paper chromatography was performed with a mixture of 0.1 M ammonium acetate and 95 percent ethanol (3:7) (pH 3.8) at room temperature in tanks flushed with nitrogen; the papers were then dried at room temperature. The adenosine triphosphate, diphosphate and monophosphate (ATP, ADP and AMP, respectively) zones were identified and cut away. The remaining material was eluted with 0.05N formic acid and lyophilized. The dried material was taken up in 5 ml of 0.05N formic acid and chromatographed on Sephadex G-25 (column, 5×83 cm). The column was washed twice with equal volumes of 0.05N formic acid and then developed with the same solution. 2.5 ml fractions were collected at a flow rate of 15 drops per minute in a fraction collector and then analyzed for absorbancy at 230 and 260 nm and for ninhydrin reactivity. The results are shown in FIG. 1.

Five fractions or peaks were identified. There was evidence for peptide throughout the chromatogram from the absorbance at 230 nm and especially in fraction 2, where the major 230 nm peak corresponded with the ninhydrin-positive peak.

Molecular sieving of the biologically active ninhydrin fraction 2 indicates that its molecular size is between 1000 to 1500 daltons. Two and sometimes three 260 nm absorption peaks eluted later and were ninhydrin-negative. When these fractions were tested in the cyclic AMP - dependent protein kinase assay, inhibitory activity appear in fractions 1 to 3; the major activity was in fraction 2, which also was the only fraction with increased inhibitory action of insulin, as compared to the control, whether the assay was performed in the presence or absence of cyclic AMP.

EXAMPLE 2

Column fraction 2 from control and insulin-treated rat skeletal muscle extracts was lyophilized and redissolved in 1 ml of 0.05N formic acid. The reaction mixture for the protein kinase assay contained (total volume=90 μl) 5 μl of inhibitor fraction, 8 mMMgCl$_2$, 120 mM morphoethanesulfonic acid (MES) buffer (pH 6.6), 0.12mM[$\gamma$—$^{32}$P] ATP (800 to 1000 cpm/pmole), 0.40 mg of histone per milliliter and, when present, 2.5 μM cyclic AMP. After 10 minutes at 30° C., 15-μl portions were pipetted onto instant thin-layer chromatography strips (ITLC;Gelman) that were then spotted with 20 percent trichloroacetic acid, 1 mM ATP, and 4 mM Pi. Strips were then chromatographed in 5 percent trichloroacetic acid containing 0.2 M KCl, and analyzed for radioactivity. The results are shown in Table I.

TABLE I

| Cyclic AMP | Inhibition of protein kinase (%) | | Net effect due to insulin (%) |
|---|---|---|---|
| | Control | Insulin | |
| None | 45.6 | 60.4 | 33 |
| Present | 52.1 | 63.0 | 21 |

EXAMPLE 3

Figure 2:
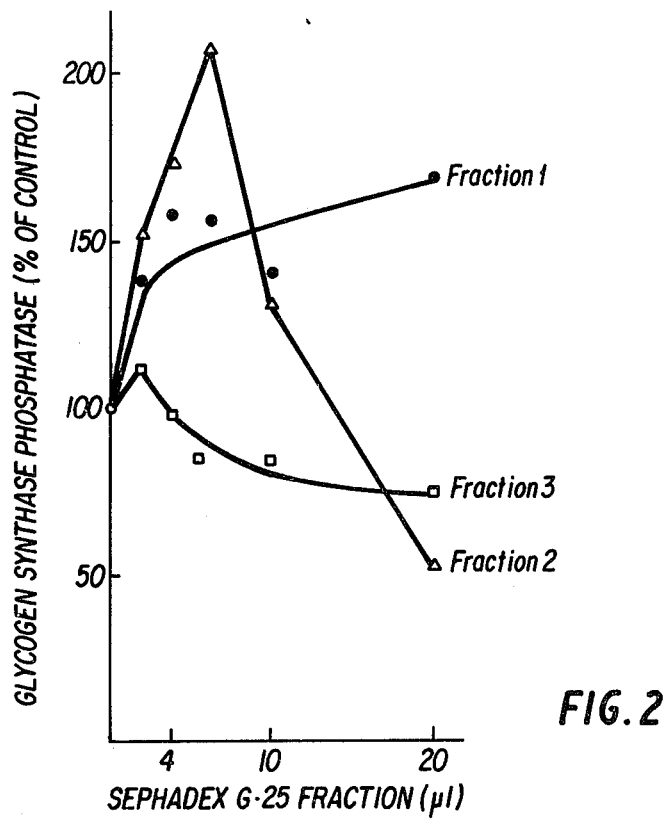
FIG. 2 shows the activation of glycogen synthase phosphoprotein phosphatase by various Sephadex G-25 column fractions.

Varying amounts of reconstituted fractions 1,2 and 3 from insulin-treated rat skeletal muscle extract were lyophilized and redissolved in 0.2 ml of 140 mM MES (pH 7.0) containing glycogen synthase D (0.2 mg/ml) and a crude glycogen synthase phosphoprotein phosphatase (2.8 mg/ml). After incubation at 21° C. for 20 minutes, 20-μl portions were removed for glycogen synthase assay in the absence and presence of glucose 6-phosphate. The reaction mixtures for the glycogen synthase assay contained (total volume=90 μl) 4.4 mM uridine diphosphate glucose, 13.3 mM EDTA, 100 mM potassium fluoride, 6.7 mg of glycogen per milliliter, 7.2 mM glucose 6-phosphate, if present, and 33 mM tris buffer (pH 7.8). The mixtures were incubated for 10 minutes at 30° C. and analyzed. The results are shown in FIG. 2.

Fractions 1 and 2 extracted from insulin-treated muscle also activated muscle phosphoprotein phosphatase in a dose-dependent manner, with fraction 2 being more potent. At higher concentrations, fraction 2 had an inhibitory effect on the phosphatase. This effect may be due to the impure nature of the material.

EXAMPLE 4

Sephadex G-25-fraction 2 was chromatographed on thin-layer chromatography cellulose sheets in a mixture of ammonium acetate and ethanol (pH 3.8). Six fractions, a to f, were eluted with 0.05N formic acid, lyophilized, redissolved in 0.05N formic acid, and assayed with cyclic AMP-dependent and -independent protein kinases. Cyclic AMP-dependent protein kinase was assayed, as in Example 2, with homogeneous protein kinase from skeletal muscle (0.01 mg/ml). Independent protein kinases were assayed by the method described in Example 2 with the following modifications: the independent kinases were assayed at pH 6.8, while phosphorylase b kinase was assayed at pH 7.4. Glycogen synthase I (0.29 mg/ml) was substrate for all the independent kinases. Cyclic AMP-independent kinases were prepared as described by DePaoli-Roach, Roach and Larner (J. Biol. Chem., in press). The enzyme PC 0.4 (phosphocellulose column fraction eluting with 0.4 M KCl) was present at a final concentration of 0.18 mg/ml; PC 0.7 at 0.09 mg/ml. The reaction mixtures contained 0.5 mM EDTA and 0.2 mM EGTA; phosphorylase b kinase was added to a final concentration of 6.3 µg/ml and $CaCl_2$ to a final concentration of 1.2 mM. The results are shown in Table II for fraction 2d.

TABLE II

| Condition | Inhibition of protein kinase (%) | | Net effect due to insulin (%) |
|---|---|---|---|
| | Control | Insulin | |
| Cyclic AMP - dependent protein kinase | | | |
| +Cyclic AMP | 70.0 | 93.0 | 33 |
| −Cyclic AMP | 38.0 | 74.0 | 95 |
| Cyclic AMP - independent protein kinase | | | |
| PC 0.4 | 70.0 | 64.0 | |
| PC 0.7 | 82.0 | 79.0 | |
| Phosphorylase b kinase | 69.0 | 68.0 | |

Further purification of fraction 2 by thin-layer chromatography produced six fractions, which were assayed. Fraction 2d, which contained the inhibitor of the cyclic AMP-dependent protein kinase, demonstrated the difference between control and insulin in the absence, as well as presence, of cyclic AMP. To determine the specificity of the protein kinase inhibition, fraction 2d was tested on three different cyclic AMP-independent protein kinases, including phosphorylase b kinase. No difference between control and insulin was observed, indicating that the material had specificity for the cyclic AMP-dependent protein kinase.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. A process for producing an insulin mediator substance comprising:
   contacting muscle tissue with insulin;
   deproteinizing the muscle tissue;
   removing the major nucleotides from the deproteinized muscle tissue;
   chromatographing the so-treated product on a Sephadex G-25 column using 0.05 N formic acid; and
   recovering the fraction wherein the major 230 nm absorbance peak corresponds with the ninhydrin-positive peak.

2. The product of the process according to claim 1.

3. The process according to claim 1, wherein deproteinization is effected by denaturing the protein and removing the denatured protein.

4. The process according to claim 1, wherein the major nucleotides adenosine triphosphate, adenosine diphosphate and adenosine monophosphate are removed.

5. The process according to claim 4, wherein removal of the major nucleotides is effected by paper chromatography.

6. The process according to claim 4, wherein removal of the major nucleotides is effected by adsorption on charcoal.

7. The process according to claim 1, further comprising the step of thin-layer chromatographing the recovered fraction wherein the major 230-nm absorbance peak corresponds with the ninhydrin-positive peak and recovering the fraction which contains an inhibitor of cyclic AMP-dependent protein kinase.

8. The product of the process according to claim 7.

9. The process according to claim 1, further comprising the step of subjecting the recovered fraction wherein the major 230-nm absorbance peak corresponds with the ninhydrin-positive peak to high voltage electrophoresis and recovering the fraction which contains an inhibitor of cyclic AMP-dependent protein kinase.

10. The product of the process according to claim 9.

* * * * *